United States Patent [19]
Spears et al.

[11] Patent Number: 5,976,119
[45] Date of Patent: Nov. 2, 1999

[54] HIGH PRESSURE PERFUSION DEVICE

[75] Inventors: J. Richard Spears, Bloomfield Hills, Mich.; Philip S. Levin, Thompson, Conn.; Paul J. Zalesky, Huntington Beach, Calif.

[73] Assignees: Wayne State University, Detroit, Mich.; TherOx, Inc., Irvine, Calif.

[21] Appl. No.: 09/138,198

[22] Filed: Aug. 21, 1998

Related U.S. Application Data

[62] Division of application No. 08/563,057, Nov. 27, 1995, Pat. No. 5,797,876.

[51] Int. Cl.[6] ................................................ A61M 25/00
[52] U.S. Cl. ........................ 604/508; 604/24; 604/26; 604/96; 604/264
[58] Field of Search ........................... 604/95, 264, 282, 604/280, 19, 49, 52, 53, 27, 200, 202

[56] References Cited

U.S. PATENT DOCUMENTS

| | | | |
|---|---|---|---|
| 5,322,508 | 6/1994 | Viera | 604/52 |
| 5,599,296 | 2/1997 | Spears | 604/26 |
| 5,797,874 | 8/1998 | Spears | 604/53 |
| 5,797,876 | 8/1998 | Spears et al. | 604/95 |

*Primary Examiner*—Corrine McDermott
*Assistant Examiner*—Kent Gring
*Attorney, Agent, or Firm*—Fletcher, Yoder & Van Someren

[57] ABSTRACT

The present invention includes a guidewire device capable of delivering perfusion fluids to a vascular site while at the same time exhibiting handling characteristics associated with existing non-perfusion guidewires. Preferred embodiments include a perfusion guidewire which closely matches the dimensions and physical characteristics of standard guidewires. Preferred embodiments also permit high pressure perfusion of supersaturated solutions, and include a liquid flow path which will not promote bubble generation or growth, or destabilize a supersaturated solution.

35 Claims, 9 Drawing Sheets

HIGH PRESSURE PERFUSION DEVICE

CROSS REFERENCE TO RELATED APPLICATIONS

This patent application is a divisional a of Ser. No. 08/563,057, filed Nov. 27, 1995, now U.S. Pat. No. 5,797,876.

FIELD OF THE INVENTION

The present invention relates generally to medical devices for the delivery of fluids transluminally, more particularly to a perfusion device, and even more particularly to a high pressure perfusion guidewire.

BACKGROUND

Various medical procedures require fluids to be delivered to specific locations within the body, typically via a fluid delivery catheter. A narrow steerable guidewire is often used to maneuver through narrow, tortuous, and/or branching body passageways. After the guidewire has been directed to the desired location, a fluid delivery catheter may be inserted over the guidewire. The guidewire is usually removed before fluid delivery begins. Guidewires which are themselves capable of fluid delivery (such as that disclosed in U.S. Pat. No. 5,322,508) are also known in the art.

During balloon angioplasty procedures, a catheter equipped with a small balloon is inserted (usually over a guidewire) into an artery that has been narrowed, typically by the accumulation of fatty deposits. The balloon is then inflated to clear the blockage or lesion and widen the artery. Upon balloon inflation, blood flow distal to (i.e., "downstream" from) the inflated balloon may be almost completely stopped.

Myocardial ischemia (i.e., a reduction in blood perfusion to the heart muscle) occurs transiently in the majority of patients undergoing coronary angioplasty procedures, such as balloon angioplasty, directional atherectomy, rotational atherectomy, and stent deployment. The permissible duration of occlusion due to balloon inflation or other device deployment is normally determined by the severity of myocardial ischemia. Typically, evidence of severe ischemia (including patient chest pain and ECG changes) requires that the operator deflate the balloon or remove the occlusive device after approximately 60 to 120 seconds. For anatomically difficult lesions, such as type B and C lesions, longer periods of balloon inflation (or other device deployment) are frequently desirable for the first balloon inflation or other device deployment.

Autoperfusion balloon catheters, and catheters of the type disclosed in U.S. Pat. No. 5,322,508, can in some circumstances allow longer periods of balloon inflation. However, the blood (or other physiologic liquid) flow through such devices is frequently insufficient to provide an adequate oxygen supply to tissues distal to the angioplasty balloon or other occlusive device.

Recent advances in the generation and application of oxygen supersaturated solutions have made it possible to deliver greater amounts of oxygen to tissues distal to an angioplasty balloon. U.S. Pat. No. 5,407,426, and pending application Ser. Nos. 08/273,652, filed Jul. 12, 1994, entitled "Method for Delivering a Gas-Supersaturated Fluid to a Gas-Depleted Site and Use Thereof"; 08/353,137, filed Dec. 9, 1994, entitled "Apparatus and Method of Delivery of Gas-Supersaturated Liquids"; 08/453,660, filed May 30, 1995, entitled "Method for Delivering a Gas-Supersaturated fluid to a Gas-Depleted Site and Use Thereof"; 08/465,425, filed Jun. 5, 1995, entitled "Method for Delivery of Gas-Supersaturated Liquids"; 08/484,279, filed Jun. 7, 1995, entitled "Apparatus and Method of Delivery of Oxygen-Supersaturated Physiologic Solutions During Clinical Procedures"; and 08/484,284, filed Jun. 7, 1995, entitled "High Pressure Gas Exchanger", which are incorporated herein by reference, disclose various methods for the generation and application of oxygen supersaturated liquids.

As is described in the above referenced patent applications, the generation, transport and delivery of oxygen supersaturated liquid may require the application of very high hydrostatic pressures. Accordingly, there remains a need for a high pressure fluid delivery device capable of infusing bubble-free fluid, which is supersaturated with oxygen, to vessels or ducts through and beyond the central lumen of a balloon angioplasty catheter or similarly occlusive device. There remains a further need for a quick connect/disconnect assembly which can withstand high pressures that may be experienced in delivering such oxygen supersaturated liquids from a fluid reservoir to a suitable fluid delivery device, and which can minimize the time required for the initiation or termination of oxygen supersaturated liquid perfusion.

SUMMARY

Accordingly, it is an object of the present invention to provide a guidewire device capable of delivering perfusion fluids to a vascular site while at the same time exhibiting handling characteristics associated with existing non-perfusion guidewires so that additional education or retraining of operators is reduced or eliminated.

Preferred embodiments of the present invention meet the foregoing needs by providing a perfusion guidewire which closely matches the dimensions and physical characteristics of standard guidewires in diameter, length, flexibility, column strength, torque transfer, surface friction, kink resistance, radiopacity (i.e., opacity to x-rays), non-thrombogenicity (i.e., tendency not to promote blood clots) and bio-compatibility. Preferred embodiments of the invention permit high pressure perfusion and also include a liquid flow path which will not promote bubble generation or growth, or destabilize the oxygen supersaturated solution.

A high pressure perfusion guidewire according to the invention preferably includes three sections: a tubular proximal segment or handle, which comprises the greater part of the perfusion guidewire length; a transitional region including a "quill-like" lip which provides the desired torque transfer and pressure drop characteristics; and a distal segment which conveys the fluid out of the perfusion guidewire, but also mimics the distal functions of a standard coronary guidewire.

The proximal segment may be connected to a fluid source using standard connectors known to those skilled in the art.

DETAILED DESCRIPTION

Figure 1:
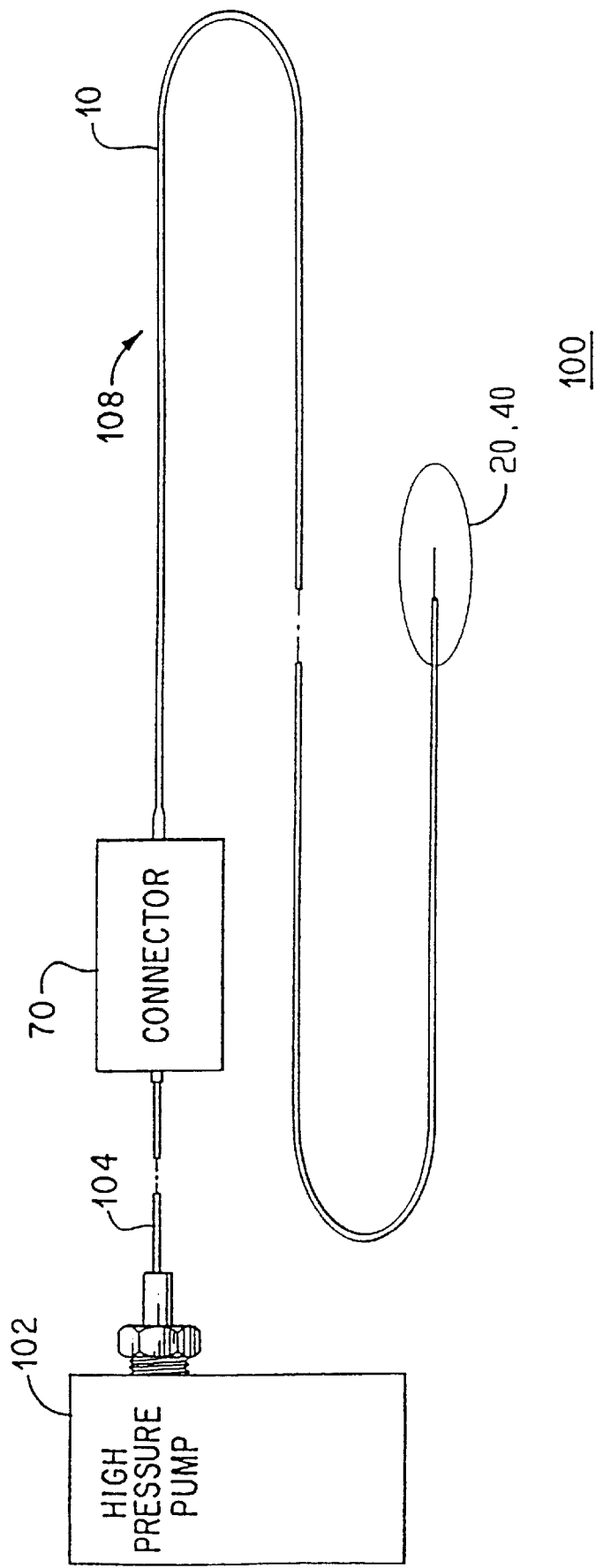
FIG. 1 shows a transluminal fluid delivery system including a high pressure perfusion device according to a preferred embodiment of the invention.

The structure and function of the preferred embodiments can best be understood by reference to the drawings. The reader will note that the same reference numerals appear in multiple figures. Where this is the case, the numerals refer to the same or corresponding structure in those figures.

The present invention includes several embodiments of a perfusion guidewire. As will be made clear below, the major differences between the various embodiments are in the transitional region and distal segments. Persons of ordinary skill in the art will understand that the alternative regions or segments may be used together in combinations other than described in detail below, based on the teachings contained herein.

Transluminal Fluid Delivery System

FIG. 1 shows a transluminal fluid delivery system 100 according to a preferred embodiment of the invention. Fluid delivery system 100 includes a high pressure source 102, such as a pump or reservoir, a connector 70, a tube 104 connecting an output of high pressure source 102 to an input of connector 70, and a perfusion guidewire 108. As will be discussed further below, each embodiment of perfusion guidewire 108 includes a handle or proximal segment 10, a transitional region 20, and a distal segment 40.

Proximal Segment or Handle

Figure 2:
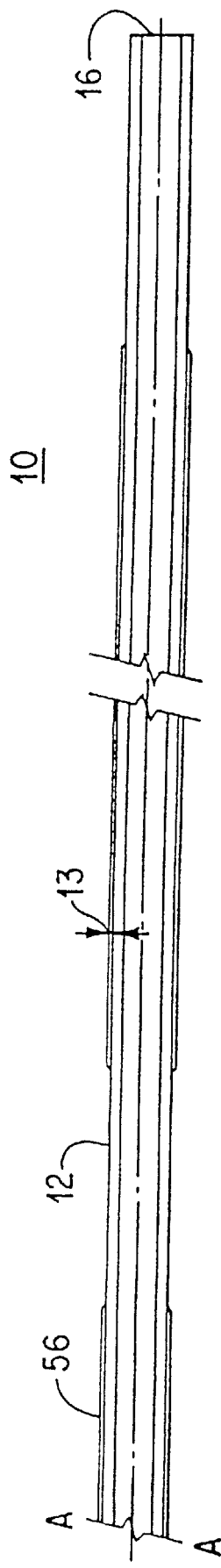
FIG. 2 is a cross sectional view of the proximal portion of a high pressure perfusion guidewire according to the invention.

Referring now to FIG. 2, a handle or proximal segment 10 of perfusion guidewire 108 is shown. Proximal segment 10 includes a thin-walled tube 12 which defines a lumen. Tube 12 is made of bio-compatible material, has the appropriate dimensions, and the appropriate burst strength, flexibility, torque transfer, and kink resistance characteristics for use as perfusion guidewire as described herein. Tube 12 is preferably coated over most of its length with a low friction, thin film bio-compatible coating 13, such as PTFE. Tube 12 also has an opening 16 for connection to a source of high pressure, oxygen supersaturated liquid.

In one embodiment, tube 12 of proximal segment 10 is preferably a 304 stainless steel tube having a 0.0145" outside diameter, a 0.010" inside diameter, and a length of approximately 150 cm. Tube 12 preferably also has a 0.0004" to 0.0007" thick coating 13 of PTFE over its full length, except for a few cm at each end. In another embodiment, tube 12 of proximal segment 10 is a 304 stainless steel tube having a 0.0132" outside diameter, a 0.008" inside diameter, and a length of approximately 150 cm. In this embodiment, tube 12 would also preferably have a 0.0004" to 0.0007" thick coating of PTFE over its full length, except for a few cm at each end. If necessary to avoid kinking during the initial part of a procedure, a support wire or stylet (not shown) may be inserted in tube 12. The support wire or stylet would be withdrawn before liquid is introduced into tube 12.

Transitional Region

Figure 3:
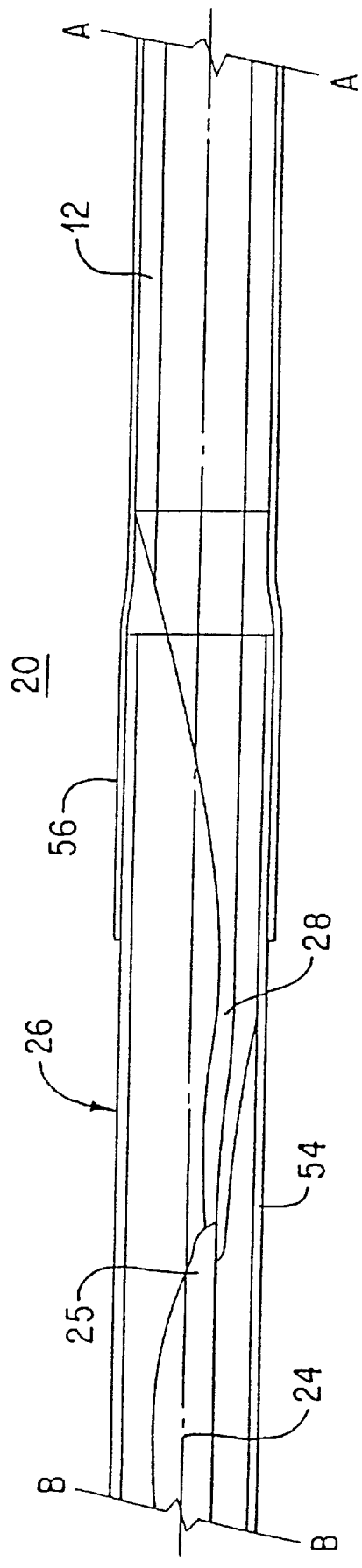
FIG. 3 is a cross sectional view of the transitional region of a high pressure perfusion guidewire according to the invention, continued from FIG. 2.

Referring now to FIG. 3, one embodiment of a transitional region 20 of perfusion guidewire 108 is shown. Transitional region 20 provides a transition between tube 12 and the region defined by core wire 24 and sheath 26. The transitional region 20 also is designed to achieve the objective of providing a perfusion guidewire with the handling characteristics of a "standard" guidewire. "Standard" guidewire is used herein to refer to the typical non-perfusion guidewires commonly used today for various procedures. Such procedures may involve coronary or peripheral vessels. Examples of guidewires considered to be standard guidewires are shown in U.S. Pat. Nos. 4,538,622 and 4,619,274. Based on the teachings contained herein, a person of ordinary skill in the art may select the various parameters of the present invention to achieve handling characteristics substantially the same as those of the above guidewires, or any other handling characteristics desired for a particular procedure.

In one embodiment, the distal end of tube 12 is ground or otherwise machined eccentrically so that a tapered lip 28 is created which resembles the nib end of a quill pen. Alternatively, a separate lip may be secured to the end of the tube. By way of example, for the tube 12 dimensions described above, lip 28 is preferably between 1 and 5 cm long, and is preferably tapered smoothly to a final dimension of 0.006" wide and 0.001" thick. This "quill-like" lip 28 provides several advantages.

First, lip 28 provides a low resistance transition, since the transition from tube 12 to the region defined by core wire 24 and sheath 26 is accomplished with little or no decrease in cross-section flow area, and in some instances even net increase. Second, lip 28 provides a smooth flow transition because lip 28 is tapered; there are no abrupt changes in the flow path geometry. These first two characteristics reduce the possibility that cavitation or bubble formation will take place in a supersaturated solution flowing through the guidewire. As a third advantage, lip 28 provides a convenient and strong attachment point for the distal core wire 24. Finally, lip 28 provides a joint between core wire 24 and tube 12 which creates a smooth transition in terms of flexibility and stiffness. The taper of lip 28 may be easily adjusted to match any desired flexibility profile. In particular, the taper may be adjusted to match the flexibility profile of a standard coronary guidewire.

An important element of guidewire design involves the transfer of torque from the proximal end of the guidewire, where the physician manipulates the guidewire, to the distal end. A smooth, even rotary action is required of a guidewire, even in a tortuous vascular pathway. Because lip 28 is not axially symmetric, it can exhibit a "cast" or unevenness in rotary motion when it is passed over a sharp bend. To reduce the cast, lip 28 is preferably sufficiently short in length and core wire 24 is long enough such that lip 28 is positioned proximal of any sharp bends in the vascular pathway during use. In practice, it is usually sufficient to locate lip 28 proximal of the aortic arch during a coronary angioplasty procedure.

Figure 4:
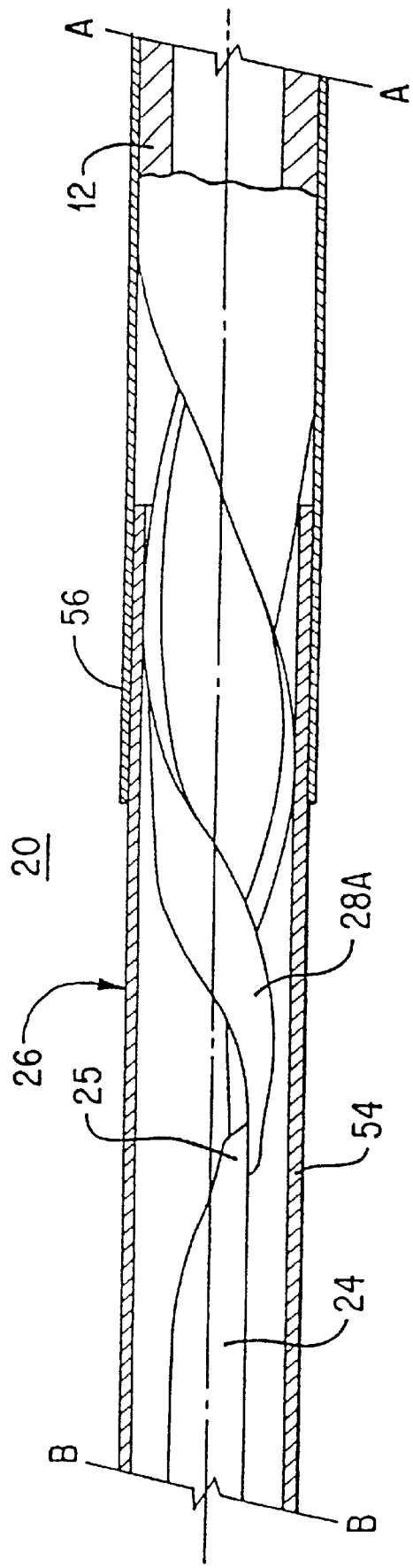
FIG. 4 is a cross sectional view of the transitional region of an alternative embodiment of a high pressure perfusion guidewire according to the invention, also continued from FIG. 2.

Referring now to FIG. 4, an alternative embodiment of transitional region 20 is shown. In procedures where transitional region 20 must encounter vascular tortuosity, or it is otherwise desirable to greatly reduce the cast, a lip 28A may be fashioned from the distal end of tube 12 into a helical form. Lip 28A will exhibit more evenness in rotary motion when passed over sharp bends than lip 28, but lip 28A will still maintain the aforementioned advantages of the non-helical lip 28. Exemplary dimensions for lip 28A with the tubes described above are 5 cm long, and tapered smoothly to a final dimension of 0.006" wide and 0.001" thick.

Distal Segment

Figure 5:
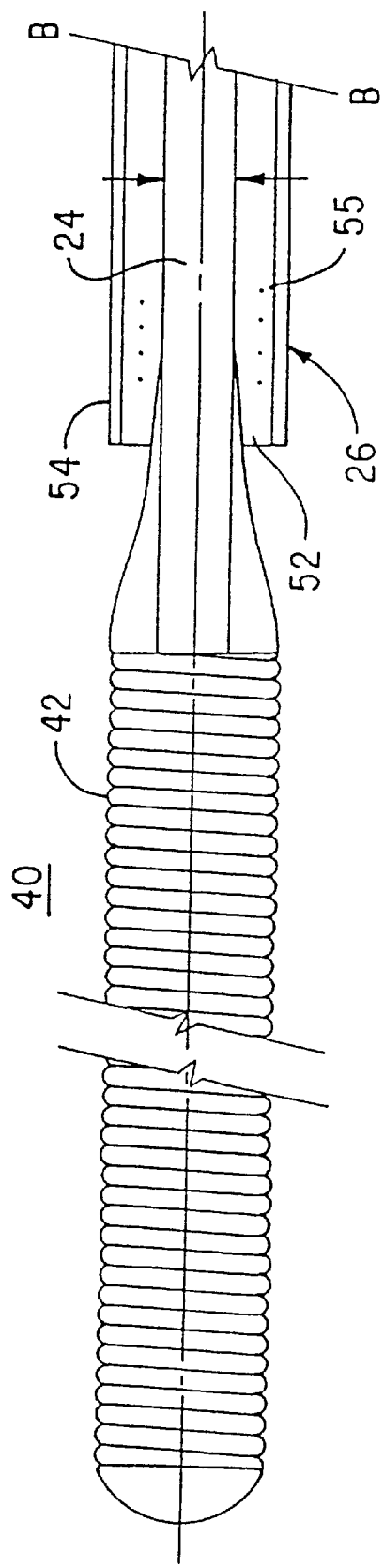
FIG. 5 is a partially cross sectional view of the distal segment of a high pressure coronary perfusion guidewire according to the invention, continued from either of FIGS. 3 or 4.

FIG. 5 shows one embodiment of a distal segment 40 of perfusion guidewire 108. Distal segment 40 includes core wire 24, thin-walled sheath 26 and a distal coil or coil spring 42. The material properties and dimensions of distal segment 40 are preferably selected to match the physical properties of standard coronary guidewires.

In an exemplary embodiment, sheath 26 comprises approximately 30 cm of high strength polymer tubing 54, having an outside diameter of about 0.0145" and an inside diameter of about 0.0135", and approximately 4 cm of polyester heat shrink tubing 56 in the transitional and proximal regions (See FIGS. 2–4) having an approximate, unrecovered inside diameter of 0.017" and a wall thickness of about 0.0005". Tubing 54 is preferably made of polyimide. At the proximal end of sheath 26, the polyimide tubing 54 is placed over lip 28 or 28A to within 1 cm of the proximal end of lip 28 or 28A. Polyester heat shrink tubing 56 forms a bridging joint between tube 12 and polyimide tubing 54. A thin epoxy film (not shown) is applied beneath heat shrink tubing 56, and then heat shrink tubing 56 is heat sealed to form a leak-free bond with tubing 12 and polyimide tubing 54.

In an alternative embodiment (shown, for example, as the proximal portion of FIG. 15), sheath 26 comprises approximately 35 cm of high strength polymer tubing 54, having an outside diameter of about 0.0145" and an inside diameter of about 0.0135". Tubing 54 is preferably made of polyimide. At the proximal end of sheath 26, the polyimide tubing 54 is placed over lip 28 or 28A and onto a portion of tube 12 proximal to lip 28 or 28A. A thin epoxy film (not shown) is applied beneath polyimide tubing 54 to form a leak-free bond with tubing 12.

The polyimide tubing 54 is preferably coated with a thin film of a lubricious hydrophilic coating. Appropriate hydrophilic coatings, such as BSI PVO1/PVP, are well known to those skilled in the art.

At its distal end, polyimide tubing 54 of sheath 26 may be open- or close-ended. If polyimide tubing 54 is close-ended, it may be configured with a number of sideports 55 or some such means to allow flow to exit sheath 26. The sideports 55 can be made as a plurality of perforations which are typically between about 15–50 μm in diameter, arranged along about a 2 cm length. The open end 52 of polyimide tubing 54 may be positioned over distal coil 42, or it may terminate before coil 42 as is shown in FIG. 5. Alternatively, the distal end of polyimide tubing 54 may overlap distal coil 42 and be bonded with epoxy to distal coil 42 as shown, for example, in FIG. 15. Polyimide tubing 54 may also be attached to an exposed portion of core wire 24. If polyimide tubing 54 is open-ended, it may be terminated with a bevel or a square cut open end 52, and may also be configured with a number of sideports 55. The actual configuration of the openings and total area can be selected by a person of ordinary skill based on the teachings herein.

As was discussed above, core wire 24 is attached at its proximal end to the distal end of lip 28 or 28A (see FIGS. 3 and 4). At its distal end, core wire 24 is embedded at least partially into distal coil 42 as is known in guidewire construction. Core wire 24 may have any appropriate cross-sectional shape, length and diameter.

In an exemplary preferred embodiment, core wire 24 is approximately 35 cm long with a circular cross section. Over the proximal 24 cm, core wire 24 has an outside diameter of about 0.006". It then tapers smoothly over a approximately 2 cm distance to an outside diameter of about 0.005", and is constant at this diameter for approximately 5 cm. Core wire 24 then tapers down to an outside diameter of about 0.003", where it is embedded within distal coil 42. Core wire 24 is ground at the proximal end to form a 3 mm long entrance taper 25 which provides a smooth flow transition from lip 28 or 28A, as discussed above (See FIGS. 3 and 4). The entrance taper 25 is typically lap-joined with an appropriate solder (such as 96.5/3.5 tin/silver solder) to lip 28 or 28A, with an overlap of about 1.5' mm. Core wire 24 is preferably coated with a thin film of an appropriate hydrophilic coating.

Distal coil 42 serves as a compliant leading edge for the atraumatic and formable guidewire. The requirements, construction and dimensions of distal coil 42 are well known to those skilled in the art. In a preferred embodiment, distal coil 42 is 4 cm long with an outside diameter of 0.010" to 0.014". Distal coil 42 is preferably coated with a thin film of an appropriate hydrophilic coating such as BSI PV01/PVP. Distal coil 42 is also preferably radiopaque along its distal 2 cm, and may have a bend or cast at its distal end to allow the physician to "steer" the guidewire along tortuous passageways.

The disclosed perfusion guidewire is preferably inserted and used in the same manner as a standard coronary guidewire using a conventional torquing handle (not shown). As is known to those skilled in the art, a torquing handle is a hollow tube with an annular screw-down clamp similar to the chuck of a drill. It is slipped over the proximal end of the guidewire and screwed down to securely hold the guidewire to allow its manipulation. The preferred embodiments of the invention exhibit substantially the same performance characteristics as a standard guidewire, and can be inserted and used with conventional instrumentation and techniques. For this reason, a perfusion guidewire according to the invention could be regularly substituted for a standard guidewire, so that in the event a perfusion need arises during a procedure, there is no need to exchange guidewires. In a typical procedure using the present invention, the perfusion guidewire is inserted into the patient's vasculature and advanced to the treatment site using known techniques. This might involve crossing a lesion for application of balloon angioplasty. However, unlike standard guidewires, when the vessel is occluded during a procedure, flow in the vessel can be maintained by perfusing fluid through the guidewire of the present invention.

Other Alternative Embodiments

As was discussed above, the present invention includes several embodiments of perfusion guidewire 108. Several alternative embodiments of transitional region 20 and distal segment 40 will be discussed below. Also, dimensions provided herein are preferred dimensions for a particular size of device as described. Persons of ordinary skill in the art may appropriately size a device by modifying the preferred dimensions without departing from the scope of the invention.

Transitional Region

Figure 6:
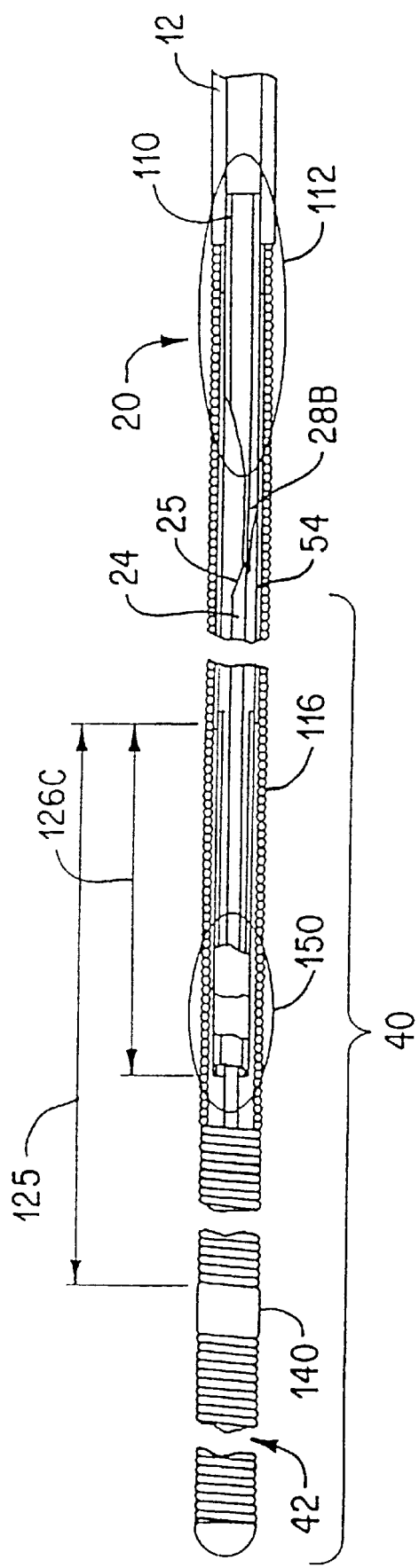
FIG. 6 is a partial cross sectional view of the transitional region and distal segment of an alternative perfusion guidewire according to the invention.
Figure 8:
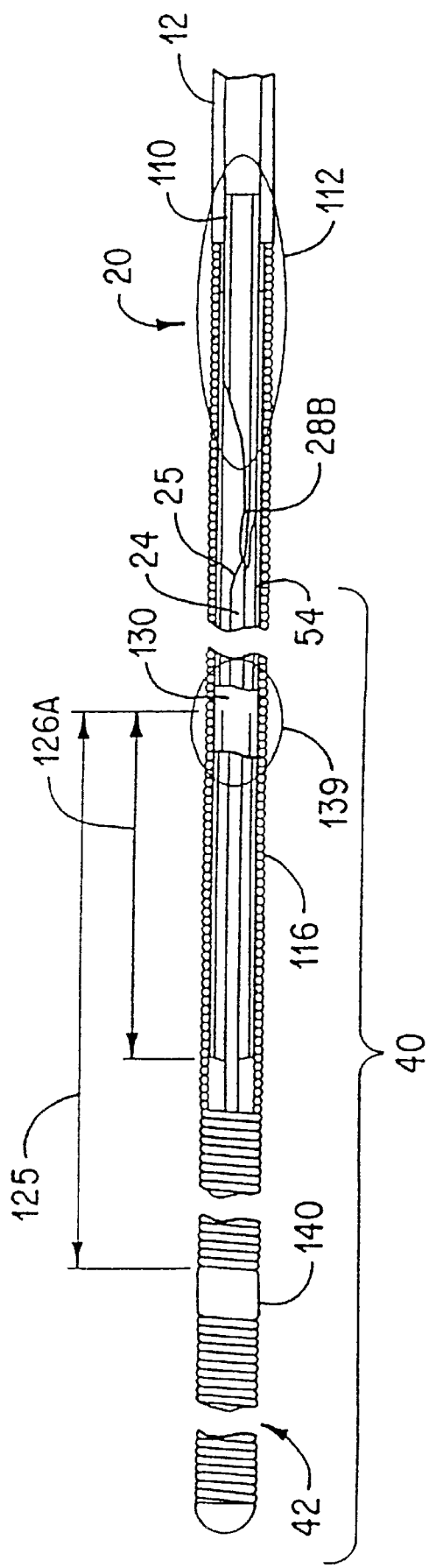
FIG. 8 is a partial cross sectional view of the transitional region and distal segment of a second alternative perfusion guidewire according to the invention.
Figure 10:
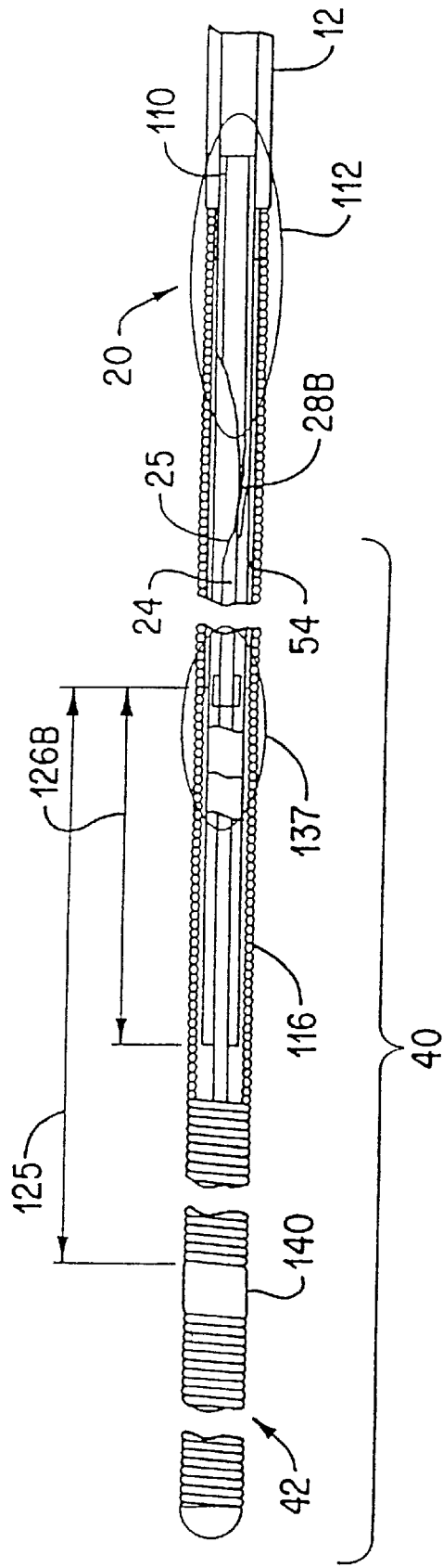
FIG. 10 is a partial cross sectional view of the transitional region and distal segment of a third alternative perfusion guidewire according to the invention.

As was discussed above with respect to FIGS. 3 and 4, transitional region 20 may include an elongated lip 28 or 28A which is formed from the distal end of tube 12. Alternatively, as is shown in FIGS. 6, 8, 10, and 12, a lip 28B may be formed from a separate tubular segment 110. By making lip 28B out of a separate tubular segment 110, the segment distal to lip 28B can be made with a substantially smaller outside diameter than would otherwise be possible if the lip were made from tube 12. Circled region 112 in FIGS. 6, 8, and 10 is shown enlarged in FIG. 12.

Figure 13:
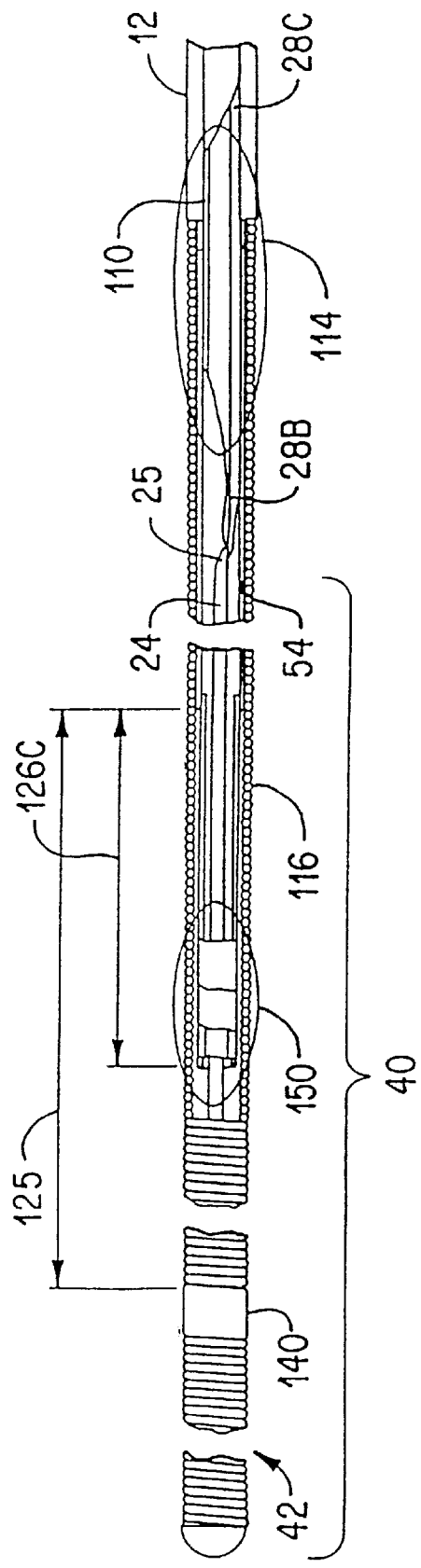
FIG. 13 is a partial cross sectional view of the transitional region and distal segment of a fourth alternative perfusion guidewire according to the invention.
Figure 14:
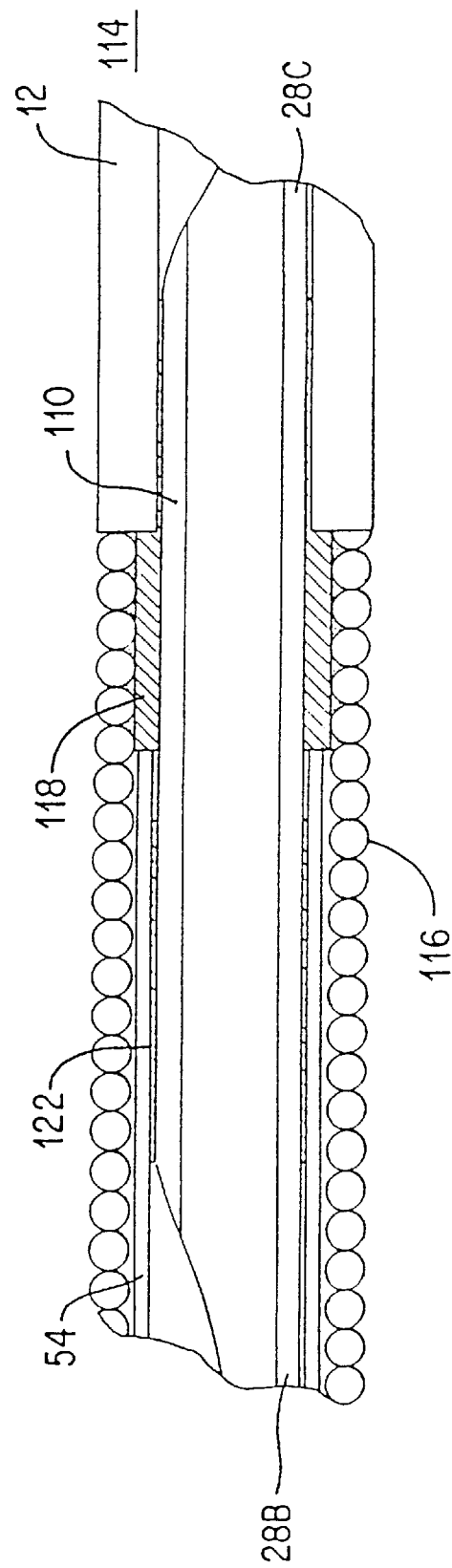
FIG. 14 is a partial cross sectional view of circled portion 114 of the distal segment shown in FIG. 13.

As is shown in FIGS. 13 and 14, tubular segment 110 may also include a second tapered lip 28C. Lip 28C provides a smooth transition from the larger inside diameter of tube 12 to the smaller inside diameter of tubular segment 110, and thus minimizes turbulence. Circled region 114 of FIG. 13 is shown enlarged as FIG. 14.

In cases where lip 28B or 28C must encounter vascular tortuosity, one or both may be fashioned into a helical form, as was discussed above with respect to FIG. 4. Lips 28B and 28C provide the same advantages as discussed above with respect to lips 28 and 28A.

Tubular segment 110 is preferably a 304 stainless steel tube having an inside diameter of 0.005", an outside diameter of 0.0075", and a length of 5 cm. Lips 28B (and where applicable 28C), are preferably approximately 1 cm long, and are preferably tapered smoothly to a final dimension of 0.006" wide by 0.001" thick.

In the embodiments shown in FIGS. 6, 8, 10, 12, 13, and 14, tubular segment 110 is typically joined to tube 12 and to stainless steel coil 116 with a lap joint 118 of an appropriate solder. Tubular segment 110 is also sealed with an overcladding or sheath of polyimide tubing 54. Polyimide tubing 54 is in turn surrounded by stainless steel coil 116, which preferably has an inside diameter of 0.010" and an outside diameter of 0.014". Polyimide tubing 54 can be sealed to tubular segment 110 via a leak tight lap bond 122 made of epoxy.

As in the above described embodiments, a core wire 24 is bonded to the distal end of lip 28B. Specifically, entrance taper 25 is preferably lap-joined with an appropriate solder to the distal end of lip 28B with an overlap of approximately 1.5 mm. Again, core wire 24 may be coated with a thin film of an appropriate hydrophilic coating.

Distal Segment

In the embodiments shown in FIGS. 6, 8, 10, and 13, distal segment 40 (i.e., the segment distal to lip 28B) generally includes core wire 24, a nonporous entrance region including tubing 54 and coil 116, a porous perfusion zone 125 including a baffle 126, and a standard floppy tip distal coil 42. Distal Coil 42 is preferably separated from coil 116 by a solid solder joint 140. Baffle 126 provides a gradual pressure and flow velocity drop for high pressure fluids being perfused.

Fluid flows from transitional region 20 through tubing 54 (and around core wire 24) to baffle 126 in perfusion zone 125. Coil 116, which surrounds and supports tubing 54 and baffle 126 allows tubing 54 and baffle 126 to withstand high hydrostatic pressures.

The perfusion zone 125 is a porous region, typically about 6 cm long, through which the perfusion fluid is delivered. To effect "weeping" or low velocity flow, perfusion zone 125 includes porous baffle 126 surrounded by stainless steel coil 116. In general, porous baffle 126 can be any suitable structure which causes a pressure (and flow velocity) drop as the fluid exits to convert high pressure fluid flow (typically at least about 250 psi) to a low velocity, or "weeping" flow. Baffle 126 preferably provides a flow velocity drop of at least one order of magnitude. The output of a low velocity, or "weeping" flow (as opposed to a flow including high velocity jets) from baffle 126 is atraumatic in that it reduces the possibility that fluid delivered by the guidewire will damage nearby tissue. A low velocity, or "weeping" flow from baffle 126 also reduces the possibility that cavitation or bubble formation will occur in the delivered fluid. As an example, at an ambient pressure of about 14.7 psi, an average blood pressure would be approximately 18 psi. Atraumatic pressure would be in this general range, but high enough to create flow. Preferably, for most applications where a pressure (and velocity) drop is required, the exit pressure will be less than about 25 psi, and the exit velocity will be less than about 200 cm/sec.

Such a pressure drop can be an important factor when high pressures are utilized with oxygen supersaturated perfusion treatments in order to maintain the oxygen partial pressure at sufficient levels downstream of a vessel-occluding procedure, such as balloon angioplasty. For example, in the delivery of oxygen supersaturated fluid according to the copending applications incorporated by reference herein, utilizing the present invention, it could be necessary to apply pressures in excess of about 1000 psi (and potentially 10,000 to 15,000 psi or higher) to ensure sufficient fluid flow and adequate oxygenation. As an example, a flow of about 35 ml per minute with perfusion of a supersaturated fluid as described in the above referenced applications can provide approximately 2 cc of oxygen per minute downstream of the treatment site in order to ensure a tissue oxygen partial pressure near acceptable levels (sustainable vessel blood flow rates typically are about 25 to 35 ml per minute in the large coronary arteries). Depending on the particular application, flow rates may be as low as about 1 ml per minute. For coronary applications, flow rates between about 10 and 50 ml per minute may be used and more specifically approximately 25 to 35 ml per minute. Oxygen can thus be delivered at rates between about 2 to 10 cc per minute and typically at least about 0.6 cc per minute. Utilizing the present invention with oxygen supersaturated fluids as described above can provide an oxygen partial pressure downstream of an occluding treatment site of at least about 75 mmHg and typically not less than about 100 mmHg. Preferable oxygen partial pressures of 1000 mmHg or greater may be achieved. Because of the high pressures that may be necessary to maintain adequate oxygen supply, the components of the invention preferably have a burst strength of at least about 1000 psi or higher to match the anticipated maximum pressures.

As shown in FIG. 6, for example, porous baffle 126 is sealed to polyimide tube 54 so that no flow can bypass porous baffle 126. Porous baffle 126 may be open or closed-ended, and preferably has length of at least approximately 2 cm. However, the length of baffle 126 may be tailored to suit the intended application, and it may be shorter than perfusion zone 125. Baffle 126 may include a polyimide tube having a plurality of fluid exit ports, one or more layers of porous polycarbonate or polyester tubing, or a combination of polyimide and polycarbonate (or polyester) tubing within coil 116. These combinations will be discussed further below.

Figure 9:
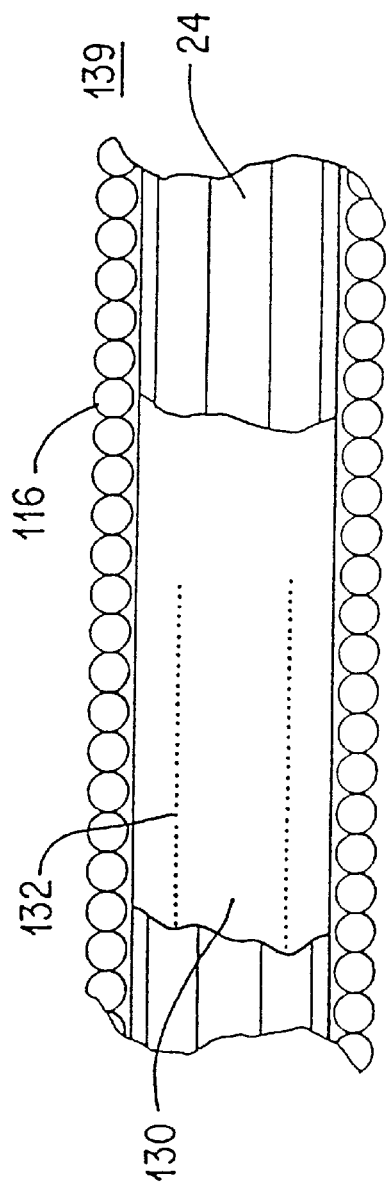
FIG. 9 is a partial cross sectional view of circled portion 139 of the distal segment shown in FIG. 8.

FIGS. 8 and 9 show a baffle 126A including a perforated polyimide tube 130. FIG. 9 is an enlarged view of the circled region 139 shown in FIG. 8. Tube 130 is perforated with a plurality of exit ports 132. Exit ports 132 may be formed with a laser, and are preferably each between 15–50 μm in diameter. Polyimide tubing 130 is surrounded by coil 116, which supports polyimide tube 130 and allows it to withstand high hydrostatic pressure. Polyimide tubing 130 may be bonded to polyimide tubing 54, or polyimide tubing 130 may be a continuous part of tubing 54. In one embodiment, the pressure of fluid exiting ports 132 causes the individual windings of coil 116 to spread apart, so that fluid may be delivered to a desired region. Alternatively, the windings of coil 116 may be pre-tensioned, during the fabrication stage, to provide a fixed spacing between the windings of between 10 and 60 microns.

Figure 11:
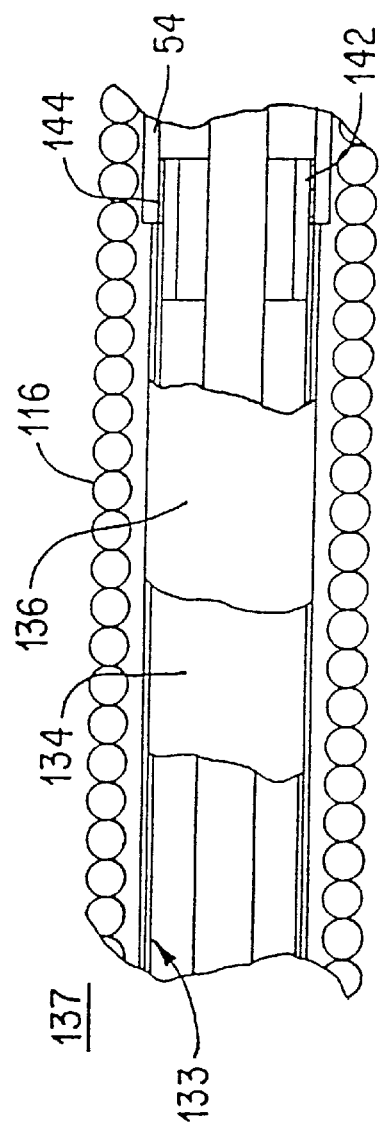
FIG. 11 is a partial cross sectional view of circled portion 137 of the distal segment shown in FIG. 10.
Figure 12:
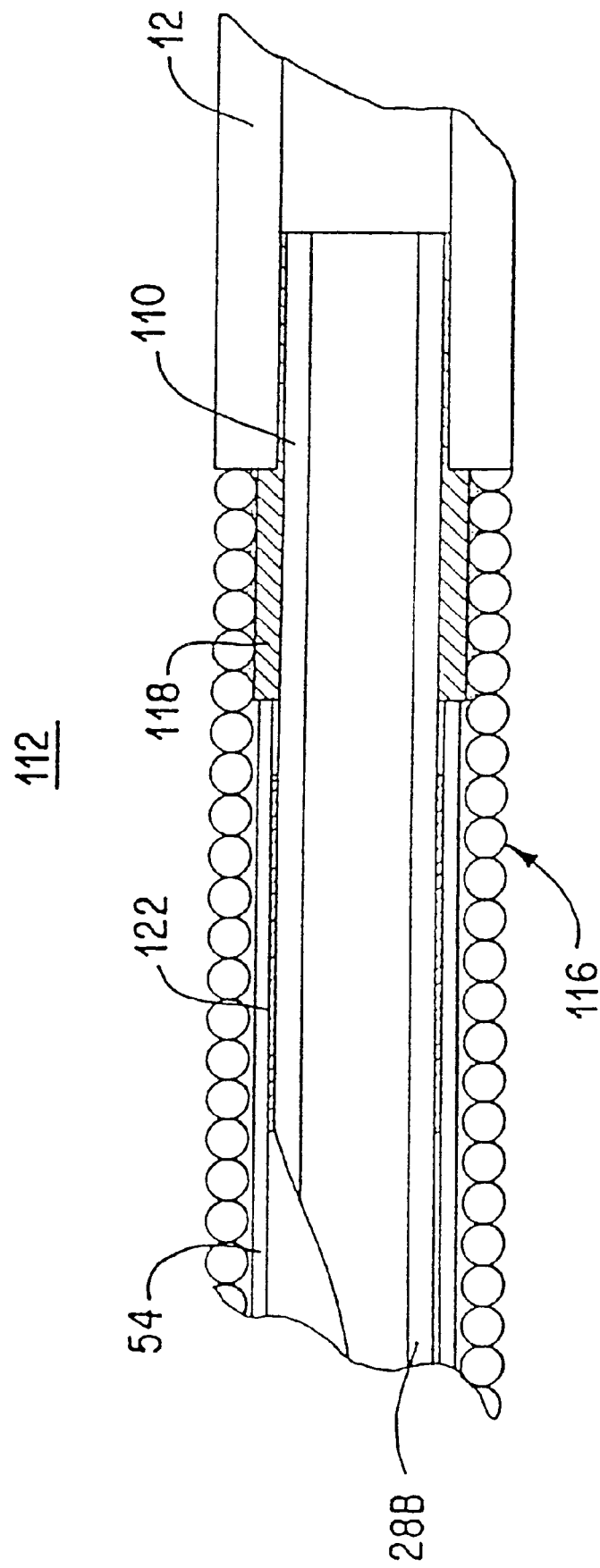
FIG. 12 is a partial cross sectional view of circled portion 112 of the transitional region shown in FIGS. 6, 8, and 10.

Referring now to FIGS. 10 and 11, a perfusion guidewire including a baffle 126B is shown. FIG. 11 is an enlarged view of the circled region 137 shown in FIG. 10. In baffle 126B, polyimide tube 54 is bonded, preferably with epoxy, to a rolled porous membrane, sheet, or tube 133 having a first ply 134 and a second ply 136. A short tubular member 142 (preferably made of polyimide) may also be used to bond polyimide tube 54 to rolled porous membrane 133. Porous membrane 133 may be any appropriate permeable material, including polyester and polycarbonate, or could be a screen or mesh of any appropriate material. A layer of epoxy 144 can be used to bond porous membrane 133 and polyimide tube 54 to tubular member 142. Plies 134 and 136 preferably have a 3 to 5 micron porosity, and are each about 6 microns thick. A single ply of porous material could also be used if desired. Additional plies of porous material will have the effect of further reducing the velocity of the delivered perfusion fluid.

Again, fluid flows out from plies 134 and 136 and then passes through the windings of stainless steel coil 116. The coils of stainless steel coil 116 may be spread apart by the hydrostatic pressure exerted by the fluid flowing from the porous membrane 133, or the windings of coil 116 may be pre-tensioned, during the fabrication stage, to provide a fixed spacing between the windings of between 10 and 60 microns.

Figure 7:
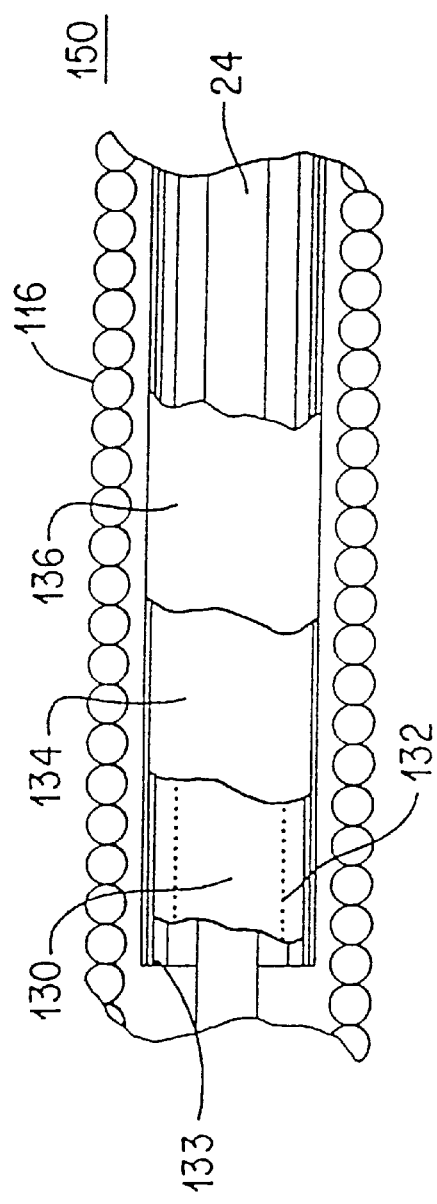
FIG. 7 is a partial cross sectional view of circled portion 150 of the distal segment shown in FIGS. 6 and 13.

Referring now to FIGS. 6, 7, and 13, a perfusion guidewire including a baffle 126C is shown. FIG. 7 is an enlarged view of circled region 150 shown in FIGS. 6 and 13. Baffle 126C preferably includes a first layer of perforated polyimide tubing 130 (including a plurality of exit ports 132) and a rolled porous membrane, tube, or sheet 133, having a first ply 134 and a second ply 136. As was discussed above with respect to the other embodiments, polyimide tubing 54 may be bonded to tubing 130 and porous membrane 133 using epoxy alone, or epoxy in combination with a separate tubular member. Tubing 130 may also form a part of tubing 54. The combination of the polyimide tube 130 with the porous membrane 133 within coil 116 reduces the possibility that high velocity jets of liquid will exit coil 116 during a perfusion procedure. Again, this ensures a low velocity, "weeping", atraumatic flow which minimizes the possibility of cavitation or bubble formation during the delivery of the oxygen supersaturated fluid, and which will minimize the possibility of damaging, or causing trauma to nearby body tissues.

Figure 15:
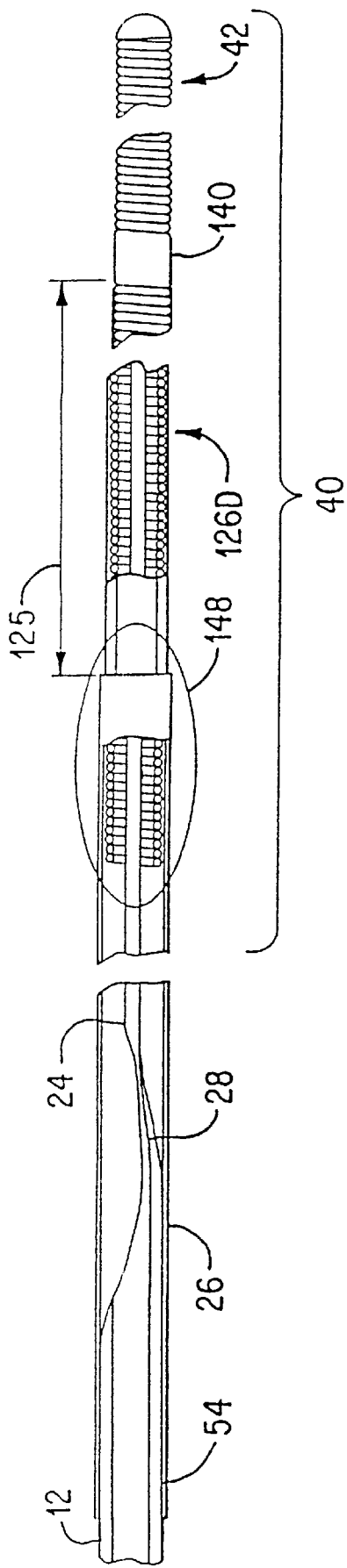
FIG. 15 is a partially cross sectional view of the transitional region and distal segment of a fifth alternative perfusion guidewire according to the invention.
Figure 16:
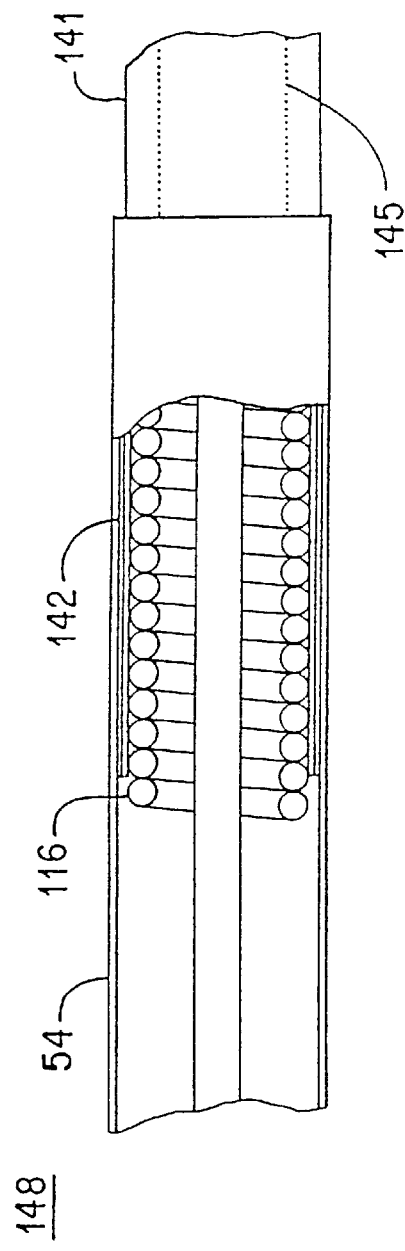
FIG. 16 is a partial cross sectional view of circled portion 148 of the transitional region shown in FIG. 15.

Referring now to FIGS. 15 and 16, an alternative embodiment of a perfusion guidewire is shown. FIG. 16 is an enlarged view of circled region 148 in FIG. 15. In FIGS. 15 and 16, polyimide tube 54 is bonded to tube 141 with a layer of epoxy 142. Tube 141 may be made of polyester heat shrink tubing, polyimide tubing, or any other suitable material. Tube 141 has a plurality of perforations 145. Thus, baffle 126D of perfusion region 125 is formed by tube 141 which fits over coil 116. In operation, fluid flows out of the windings of coil 116, and then out of perforations 145. Again, windings of coil 116 may be forced apart by the hydrostatic pressure of the fluid being delivered, or the windings of coil 116 may be pre-tensioned during the fabrication stage.

The present invention has been described in terms of a preferred embodiment. The invention, however, is not limited to the embodiment depicted and described. Rather, the scope of the invention is defined by the appended claims.

What is claimed is:

1. A method for vascular perfusion in combination with an associated vascular procedure utilizing a perfusion guidewire, comprising:
   inserting a guidewire into a patient's vasculature, the guidewire defining a perfusion lumen with a fluid exit and having an atraumatic tip;
   advancing the guidewire through the patient's vasculature to a treatment site within a vessel of interest;
   conducting a procedure at the treatment site involving at least partial occlusion of the vessel of interest; and
   introducing oxygen supersaturated fluid into the vessel of interest through the guidewire.

2. The method according to claim 1, comprising introducing the oxygen supersaturated fluid into the guidewire at a pressure of at least about 250 psi and providing a flow velocity drop at the fluid exit to an atraumatic velocity.

3. The method according to claim 2, wherein the exit velocity of the oxygen supersaturated fluid is less than about 200 cm/sec.

4. The method according to claim 2, wherein the delivery rate of the oxygen supersaturated fluid provides a partial pressure of oxygen immediately downstream of the treatment site of at least about 100 mmHg.

5. The method according to claim 4, wherein said step of conducting a procedure comprises advancing a balloon angioplasty catheter over said guidewire to the treatment site and performing balloon angioplasty at the treatment site.

6. The method according to claim 4, wherein said step of conducting a procedure comprises advancing a stent delivery catheter over said guidewire to the treatment site and deploying the stent at the treatment site.

7. The method according to claim 4, wherein the vessel of interest is a coronary artery.

8. The method according to claim 7, further comprising substantially preventing bubble formation during fluid delivery to the coronary artery.

9. The method according to claim 2, wherein the delivery rate of oxygen is at least about 0.6cc per minute.

10. The method according to claim 2, wherein the recited steps are performed in the recited order.

11. A method of vascular perfusion comprising the acts of:
   (a) coupling a source of oxygen supersaturated fluid to a guidewire disposed within a patient's vaculature, the guidewire having a lumen with a fluid exit; and
   (b) introducing oxygen supersaturared fluid from the source into the patient's vasculature through the fluid exit of the guidewire.

12. The method, as set forth in claim 11, wherein act (a) comprises the act of coupling the source of oxygen supersaturated fluid to a connected coupled to a proximal end of the guidewire.

13. The method, as set forth in claim 11, wherein act (b) comprises the act of introducing the oxygen supersaturated fluid into the guidewire at a pressure of at least about 250 psi and providing a flow velocity drop at the fluid exit to an atraumatic velocity.

14. The method, as set forth in claim 11, wherein act (b) comprises the acts of:

introducing the oxygen supersaturated fluid into the guidewire at a pressure of at least about 250 psi; and exiting the oxygen supersaturated fluid from the fluid exit of the guidewire at a pressure of less than about 25 psi.

15. The method, as set forth in claim 11, wherein act (b) comprises the act of providing a porous baffle proximate the fluid exit.

16. The method, as set forth in claim 11, wherein act (b) comprises the act of passing the oxygen supersaturated fluid through a porous baffle located within the lumen proximate the fluid exit.

17. The method, as set forth in claim 11, wherein act (b) comprises the act of introducing the oxygen supersaturated fluid into the guidewire at a pressure of at least about 1000 psi and providing a flow velocity drop at the fluid exit to an atraumatic velocity.

18. The method, as set forth in claim 11, wherein the delivery rate of the oxygen supersaturated fluid provides a partial pressure of oxygen proximate the fluid exit of at least about 100 mmHg.

19. The method, as set forth in claim 11, wherein the delivery rate of oxygen is at least about 0.6 cc per minute.

20. The method, as set forth in claim 11, wherein act (b) comprises the act of substantially preventing bubble formation during delivery of the oxygen supersaturated fluid.

21. The method, as set forth in claim 11, further comprising the act of manufacturing the guidewire for accomplishing acts (a) and (b).

22. The method, as set forth in claim 11, wherein acts (a) and (b) are performed in the recited order.

23. A method of vascular perfusion comprising the acts of:

(a) coupling a source of fluid to a guidewire disposed within a patient's vasculature, the guidewire having a lumen with a fluid exit;

(b) introducing fluid from the source into the guidewire at an introduction pressure of at least about 250 psi; and (c) delivering fluid to the patient's vasculature through the fluid exit of the guidewire at a delivery pressure that is at least an order of magnitude lower than the introduction pressure.

24. The method, as set forth in claim 23, wherein act (a) comprises the act of coupling the source of fluid to a connector coupled to a proximal end of the guidewire.

25. The method, as set forth in claim 24, wherein acts (a), (b), and (c) are performed in the recited order.

26. The method, as set forth in claim 23, wherein act (a) comprises the act of coupling a source of oxygen supersaturated fluid to the guidewire.

27. The method, as set forth in claim 26, wherein the delivery rate of the oxygen supersaturated fluid provides a partial pressure of oxygen proximate the fluid exit of at least about 100 mmHg.

28. The method, as set forth in claim 26, wherein the delivery rate of oxygen is at least about 0.6 cc per minute.

29. The method, as set forth in claim 23, wherein act (b) comprises the act of introducing the fluid into the guidewire at a introduction pressure of at least about 1000 psi.

30. The method, as set forth in claim 23, wherein act (c) comprises the act of providing a flow velocity drop at the fluid exit to an atraumatic velocity.

31. The method, as set forth in claim 23, wherein act (c) comprises the act of:

delivering the fluid from the fluid exit of the guidewire at a pressure of less than about 25 psi.

32. The method, as set forth in claim 23, wherein act (c) comprises the act of providing a porous baffle proximate the fluid exit.

33. The method, as set forth in claim 23, wherein act (b) comprises the act of passing the fluid through a porous baffle located within the lumen proximate the fluid exit.

34. The method, as set forth in claim 23, wherein act (c) comprises the act of substantially preventing bubble formation during delivery of the fluid.

35. The method, as set forth in claim 23, further comprising the act of manufacturing the guidewire for accomplishing acts (a), (b), and (c).

* * * * *

United States Patent and Trademark Office
CERTIFICATE OF CORRECTION

PATENT NO : 5,976,119

DATED : November 2, 1999

INVENTOR(S) : J. Richard Spears, Philip S. Levin, and Paul J. Zalesky

It is certified that error appears in the above-identified patent and that said Letters Patent are hereby corrected as shown below:

The title should read:

--METHOD FOR VASCULAR PERFUSION--

Signed and Sealed this

Twenty-fifth Day of July, 2000

Attest:

Q. TODD DICKINSON

*Attesting Officer*  *Director of Patents and Trademarks*